United States Patent
Mayr et al.

(10) Patent No.: US 10,314,675 B2
(45) Date of Patent: Jun. 11, 2019

(54) METHOD OF MAKING A CUSTOMIZED DENTAL BLANK

(71) Applicant: 3M INNOVATIVE PROPERTIES COMPANY, St. Paul, MN (US)

(72) Inventors: Helmar B. Mayr, Kaufering (DE); Malte Korten, Moorenweis (DE); Gallus Schechner, Herrsching (DE)

(73) Assignee: 3M Innovative Properties Company, St. Paul, MN (US)

( * ) Notice: Subject to any disclaimer, the term of this patent is extended or adjusted under 35 U.S.C. 154(b) by 154 days.

(21) Appl. No.: 15/327,772

(22) PCT Filed: Jul. 23, 2015

(86) PCT No.: PCT/US2015/041694
§ 371 (c)(1),
(2) Date: Jan. 20, 2017

(87) PCT Pub. No.: WO2016/014766
PCT Pub. Date: Jan. 28, 2016

(65) Prior Publication Data
US 2017/0209244 A1 Jul. 27, 2017

(30) Foreign Application Priority Data
Jul. 25, 2014 (EP) ..................................... 14178616

(51) Int. Cl.
*A61C 13/00* (2006.01)
*A61C 13/08* (2006.01)
(Continued)

(52) U.S. Cl.
CPC .............. *A61C 13/082* (2013.01); *A61B 1/24* (2013.01); *A61C 9/004* (2013.01); *A61C 13/0004* (2013.01); *A61C 13/0022* (2013.01)

(58) Field of Classification Search
CPC ... A61C 13/082; A61C 9/004; A61C 13/0004; A61C 13/0022; A61B 1/24
See application file for complete search history.

(56) References Cited

U.S. PATENT DOCUMENTS

| 5,151,044 A | 9/1992 | Rotsaert |
| 5,800,164 A * | 9/1998 | Pfau ..................... A61C 13/082 433/203.1 |

(Continued)

FOREIGN PATENT DOCUMENTS

| DE | 19944130 | 4/2001 |
| EP | 2799032 | 11/2014 |

(Continued)

OTHER PUBLICATIONS

International Search Report for PCT International Application No. PCT/US2015/041694 dated Sep. 17, 2015, 3 pages.

*Primary Examiner* — Nicholas D Lucchesi

(57) ABSTRACT

A method of making a customized dental blank. The method has steps of obtaining from a dental practitioner a first color scheme and a different second color scheme as well as a first dimensional information for the first color scheme and a different second dimensional information for the second color scheme. The first and second dimensional information each relate to a size and/or a location within dimensions of the dental blank. The method further has the step of manufacturing the customized dental blank which has a first portion based on the first dimensional information according to the first color scheme and a second portion based on the second dimensional information according to the second color. Further the method has the step of providing the dental practitioner with the customized dental blank. The method helps facilitating the making of a dental restoration from a blank.

14 Claims, 3 Drawing Sheets

(51) Int. Cl.
*A61B 1/24* (2006.01)
*A61C 9/00* (2006.01)

(56) References Cited

U.S. PATENT DOCUMENTS

| | | | | |
|---|---|---|---|---|
| 6,398,554 | B1* | 6/2002 | Perot | A61C 13/0004 433/223 |
| 6,951,459 | B2* | 10/2005 | Weinstein | A61C 13/082 433/26 |
| 7,035,702 | B2* | 4/2006 | Jelonek | A61C 13/0004 700/97 |
| 8,425,973 | B2* | 4/2013 | Dunne | A61C 13/0004 118/500 |
| 8,541,329 | B2 | 9/2013 | Ritzberger | |
| 9,827,076 | B2* | 11/2017 | Korten | A61C 13/0004 |
| 10,028,810 | B2* | 7/2018 | Korten | A61B 1/051 |
| 2003/0224318 | A1 | 12/2003 | Weinstein | A61C 13/082 433/26 |
| 2005/0089822 | A1* | 4/2005 | Geng | A61C 13/0004 433/215 |
| 2006/0008777 | A1* | 1/2006 | Peterson | A61C 13/0004 433/223 |
| 2006/0084027 | A1* | 4/2006 | Weinstein | A61C 13/082 433/26 |
| 2006/0257824 | A1* | 11/2006 | Pfeiffer | A61C 13/0004 433/218 |
| 2007/0065780 | A1* | 3/2007 | Dorsman | A61K 6/0023 433/215 |
| 2008/0026353 | A1* | 1/2008 | Chyz | G09B 23/283 434/263 |
| 2009/0087817 | A1* | 4/2009 | Jansen | A61C 13/0004 433/223 |
| 2010/0260924 | A1* | 10/2010 | Karim | A61C 13/0019 427/2.26 |
| 2012/0285019 | A1* | 11/2012 | Schechner | A61C 13/0004 29/896.1 |
| 2014/0372085 | A1* | 12/2014 | Korten | A61C 13/0004 703/1 |
| 2015/0335407 | A1* | 11/2015 | Korten | A61C 13/0004 433/203.1 |
| 2016/0067018 | A1* | 3/2016 | Korten | A61B 1/051 433/29 |
| 2016/0338806 | A1* | 11/2016 | Nazzal | A61C 13/0022 |
| 2017/0157645 | A1* | 6/2017 | Wolz | A61C 13/0004 |
| 2017/0209244 | A1* | 7/2017 | Mayr | A61C 13/0022 |
| 2017/0319305 | A1* | 11/2017 | Rolf | A61C 13/082 |
| 2018/0116772 | A1* | 5/2018 | Korten | A61C 13/0004 |

FOREIGN PATENT DOCUMENTS

| | | |
|---|---|---|
| WO | WO 2002-09612 | 2/2002 |
| WO | WO 2008-083358 | 7/2008 |
| WO | WO 2013-122662 | 8/2013 |
| WO | WO 2013-122663 | 8/2013 |
| WO | WO 2013-181262 | 12/2013 |

* cited by examiner

METHOD OF MAKING A CUSTOMIZED DENTAL BLANK

FIELD OF THE INVENTION

The invention relates to a method of making a customized dental blank, in particular a dental blank having a first portion based on first dimensional information according to a first color scheme and a second portion based on second dimensional information according to a second color scheme.

BACKGROUND ART

The preparation of dental restorations often includes milling or grinding the restoration from a dental blank that has a standardized size and shape. Such blanks are typically available in different tooth colors and may be selected in accordance with a particular tooth color of a patient's teeth.

Typically a dentist prepares a tooth to be restored in a patient's mouth, sends a dental impression from the patient's dentition along with tooth color information to a dental lab and obtains the finished dental restoration from the dental lab. The dental lab typically holds a stock of dental blanks from which an appropriate blank is selected for making the dental restoration. The size of the stock and the selection is always a compromise. On the one hand the stock size is desirably small but large enough to have an appropriate blank for many different dental restorations available. On the other hand the selection should be such that tolerances, in particular regarding the color, between the blank and the tooth color information obtained from the dentist are accepted but kept within limits. The making of dental restorations having rare colors or color compositions thus is particularly difficult to address and may require either a relatively large stock or the acceptance of large tolerances.

There are further approaches for providing individualized dental blanks WO 2013/122662 for example discloses a dental milling block comprising a dental article having an outer surface, the dental article having been produced based on personalized data, wherein the outer surface of the dental article is at least partially covered with a surrounding material.

The invention further relates to a process of producing a dental milling block, the process comprising the steps of: a) providing a personalized Data Set C containing geometry data of the dental article and color data related to said geometry data, b) generating a layer of hardenable material on a surface, c) applying a color agent to the layer of hardenable material of step b), wherein the color agent is applied to at least some regions of those areas of the layer of hardenable material which are related to the geometry data of the dental article, d) consolidating the result obtained in step c) thereby obtaining an at least partially hardened layer of material.

Although the current approaches for manufacturing of dental restorations may provide a variety of advantages, there is still a desire for a method of manufacturing dental restorations in a cost efficient manner and at a good aesthetic quality.

SUMMARY OF THE INVENTION

The invention relates to a method of making a customized dental blank. The method comprises the steps of:
obtaining from a dental practitioner a first color scheme and a different second color scheme as well as a first dimensional information for the first color scheme and a different second dimensional information for the second color scheme, wherein the first and second dimensional information each relate to a size and/or a location within dimensions of the dental blank;
manufacturing the customized dental blank having a first portion based on the first dimensional information according to the first color scheme and a second portion based on the second dimensional information according to the second color scheme; and
providing the dental practitioner with the customized dental blank.

The invention is advantageous in that it provides dental blanks from which two or more differently colored dental restorations are obtainable. This allows for example to provide a plurality of differently colored blank portions in one blank. Even not making use of all blank portions such blank may be less expensive and space consuming than a number of individual blanks providing the same amount of colors.

A dental practitioner for the purpose of the present invention may be a dentist, a dental technician of a dental assistant, for example. The dental practitioner may perform the determination of the first and second color scheme by use of a shade guide. In particular the dental practitioner may visually compare the shade guide having several different color samples with a tooth adjacent or opposite a tooth to be restored. The dental practitioner may determine the first color scheme according to a color sample which matches one portion of the tooth best and the second color scheme according to a different color sample which matches another portion of the same tooth best. Further, the dental practitioner may visually compare the shade guide with a first tooth and a second tooth in a patient's mouth. The dental practitioner may determine the first color scheme according to a color sample which matches the first tooth best and the second color scheme according to a different color sample which matches the second tooth best.

In one embodiment at least one of the first and second color scheme comprises a color gradient or consists of a single color. Accordingly a color scheme as referred to in this specification may be a single color only or a gradient formed of multiple colors.

In an embodiment the method further comprises the step of obtaining first dimensions of the first portion and second dimensions of the second portion from the dental practitioner. The method may further comprise the step of obtaining material information from the dental practitioner. The material information preferably relates to a material the dental blank is made of. The material may be selected from among a ceramic, a glass ceramic or a composite material, in particular selected from among zirconia, alumina, lithium disilicate, resin nano ceramic, and hybrid materials. Accordingly appropriate information for making a blank which is customized regarding the color configuration and the material may be obtained from the dental practitioner.

In one embodiment the method comprises the step of obtaining from a plurality of dental practitioners first color schemes and different second color schemes and corresponding first dimensional information and second dimensional information. Accordingly different customized dental blanks can be provided to different dental practitioners.

In a further embodiment the method comprises the step of providing a dental blank-configurator allowing at least the selection of the first and second color scheme from a plurality of pre-defined color schemes. Such dental blank-configurator may be computer-based, for example provided via the Internet. The blank-configurator may be configured to display an assortment of different blank types. Such different blank types may comprise blanks of a different three-dimensional size and/or shape, for example. Further the blank-configurator may be configured to display a variety of different tooth colors. The blank-configurator may be configured such that a user of the configurator can select the blank from the displayed blank types and at least two colors associated with the selected blank. The blank-configurator may be further configured to accept user input regarding the first and second dimensional information. Dimensional information may comprise information about the size, shape and/or location of a portion within the blank which is associated with the first, second or further color scheme. The blank-configurator may be adapted such that a configuration entered by the dental practitioner can be sent to the blank manufacturer, for example via the Internet.

In a further embodiment the method further comprises the steps of:

assigning the customized dental blank an individual code based on at least the first and second color scheme and the first and second dimensional information;

providing the customized dental blank with the individual code in a machine readable form; and controlling machining of the blank using machining instructions that are based on the individual code.

In this embodiment the individual code preferably comprises at least the first and second dimensional information. The machine used for machining the blank is preferably adapted to read the individual code, to decode the individual code and to control the machining in accordance with the first and second dimensional information. For example the individual code may be stored in a memory of an integrated circuit attached to the dental blank and the machine may have an electronic reader to read that memory. In one example an RFID tag may be used to store the individual code and an RFID reader of the machine may be configured to read the RFID tag. The individual code may comprise all information necessary to machine the dental restoration except for the data relating to the individual shape of the dental restoration. The skilled person will recognize other possibilities of providing the dental blank with the individual code. For example a bar code, OCR letters or magnetic storage media may be used.

In a further embodiment the first portion and the second portion are spaced from each other with a third portion extending between the first portion and the second portion. Further at least one of the first and second portion is/are shaped based on a dental arc or partial dental arc. Thus a variety of differently configured dental blanks can be made available.

In a further aspect the invention relates to a method of making a dental restoration. The method comprises the steps of:

providing a customized dental blank according to the invention;

capturing at least one natural tooth color from a patient's dentition; and determining the first and/or second color scheme based on the at least one natural tooth color.

The natural tooth color may be captured directly, for example using a color measuring device, or indirectly, for example by matching using a tooth color shade guide.

In one embodiment the method further comprises the steps of:

capturing the shape of at least part of the patient's dentition;

designing a dental restoration based on the captured shape; and machining the dental restoration.

For capturing the shape of at least part of the patient's dentition an intra-oral scanner may be used. Such a scanner may be configured to measure the natural tooth color of the patient's teeth. Alternatively a separate color measuring device may be used. The design of the dental restoration id preferably preformed using a CAD system that is configured to provide a computer representation of the dental restoration in the form of data to an automated manufacturing system. The automated manufacturing system, for example a CNC milling or grinding machine, is preferably configured to automatically machine the dental restoration based on the computer representation in data form.

The invention further relates to a system for making a customized dental blank. The system comprises:

a scanner for capturing the shape of at least part of the patient's dentition;

a computer being configured to receive input about a natural tooth color associated to the patient's dentition;

software configured to receive a first color scheme and a different second color scheme based on the natural tooth color;

the software being further configured to receive a first dimensional information for the first color scheme and a different second dimensional information for the second color scheme within dimensions of the dental blank;

the software being further configured to initiate, by data transfer, an order of the customized dental blank based on the first and second color scheme and the first and second dimensional information.

DETAILED DESCRIPTION OF THE INVENTION

Figure 1:
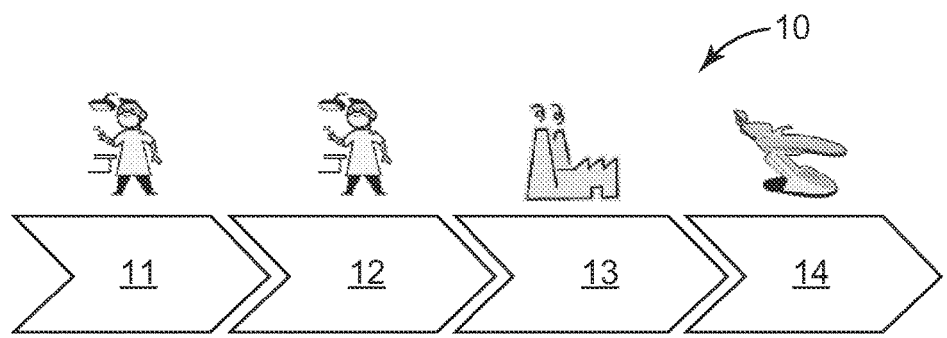
FIG. 1 is a diagram illustrating an embodiment of the method of the invention.

FIG. 1 illustrates an exemplary method 10 according to the invention. The method 10 generally allows a dental practitioner to obtain an individually colored dental blank from a blank manufacturer. The individual colors of the blank may for example be associated to two or more dental restorations for a single patient or to two or more dental restorations of multiple patients. In this regard a dental restoration may be a dental crown and/or dental bridge which can be machined (for example milled or ground) from the individual blank. The individual colors of the blank colors may be determined as follows.

In a step 11 a first color scheme and a different second color scheme are determined. In particular a dental practitioner may determine one or more tooth colors of one or more teeth in a patient's mouth. For example a patient may have a tooth to be restored and the dental practitioner may determine the color of that tooth and/or the color of a tooth neighboring the tooth to be restored. The dental practitioner may perform the determination of the one or more tooth colors by use of a shade guide. Such a shade guide is for example available under the designation VITA classical A1-D4 Shade Guide from VITA Zahnfabrik, Germany. Alternatively or additionally the dental practitioner may perform the determination of the one or more tooth colors by use of color measuring device. Such a color measuring device is for example available under the designation VITA Easyshade® Advance 4.0. The shade guide or color measuring device typically provides the tooth color in the form of a color code, for example A1, A2, A3 . . . D4. If a shade guide is used color samples of the shade guide may be compared with a color of a natural tooth in the patient's mouth and the color code of the color sample which matches the color of the natural tooth best is the color code provided via the shade guide. The color measuring device may in contrast display the color code corresponding to a natural tooth color measured by the device.

The dental practitioner may directly use two colors determined in a patient's mouth as the first and second color scheme. However the dental practitioner may further select a different color based on the determined color and use the selected color as the first and/or second color scheme. The dental practitioner may for example select the next brighter or darker color code of the color code determined in the patient's mouth.

In one example the dental practitioner determines a first tooth color of a tooth in a first patient's mouth and a different second tooth color of a tooth in a second patient's mouth wherein the dental practitioner uses the first tooth color as the first color scheme and the second tooth color as the second color scheme. In this example the first and second color scheme each are formed by a single color only. The dental practitioner may however in another example determine a color gradient based on one or more tooth colors of a tooth in a patient's mouth. This color gradient (or two different color gradients) may then be used as the first or second color scheme (or as the first and second color scheme, respectively). For example based on a determined natural tooth color A2 the dental practitioner may determine a color gradient from A2 to A3. This may provide a color shading which relatively pleasantly resembles a natural tooth.

Once the dental practitioner has determined the first and second color scheme (and eventually further color schemes) the dental practitioner in step 12 further determines a first dimensional information for the first color scheme and a different second dimensional information for the second color scheme. For example if a patient is intended to be provided with a dental crown the dental practitioner may assign the first color scheme a three-dimensional size of for example 12 mm×12 mm×12 mm of a cube shape. Other sizes are possible as appropriate. Further if that patient or a further patient is intended to be provided with a dental bridge the dental practitioner may assign the second color scheme a three-dimensional size of for example 12 mm×12 mm×24 mm of a cuboid shape. Other sizes and shape are possible. For example for larger dental bridges a three-dimensional shape corresponding to an arch extending at a certain cross-section may be used. It is noted that the step of determining the first and second color scheme and the step of determining the first and second dimensional information, respectively, are exchangeable in the order in which they are performed.

The dental practitioner may further assign the first and second color scheme a particular location in a blank. The dental practitioner may for example be provided with one or more three-dimensional standard shapes of blanks. Based on those the dental practitioner may determine a first particular location for the first color scheme and a different second particular location for the second color scheme within the, or one of the, standard blank shapes.

The first and second color scheme and the first and second dimensional information in step 13 are obtained by a blank manufacturer. For example the dental practitioner may send the first and second color scheme and the first and second dimensional information via data transmission (for example via the Internet) to the blank manufacturer.

The blank manufacturer may prepare one or more dental blanks according to the first and second color scheme and the first and second dimensional information obtained from the dental practitioner. This may be performed for example by using a build-up system in which powder material of different colors are used to build up the blank. A method and system for building up a blank from a powder is for example disclosed in patent application WO 2013/181262 A1.

In step 14 the dental blank is provided to the dental practitioner or to a dental lab for machining the dental restoration from the blank.

Figure 2:
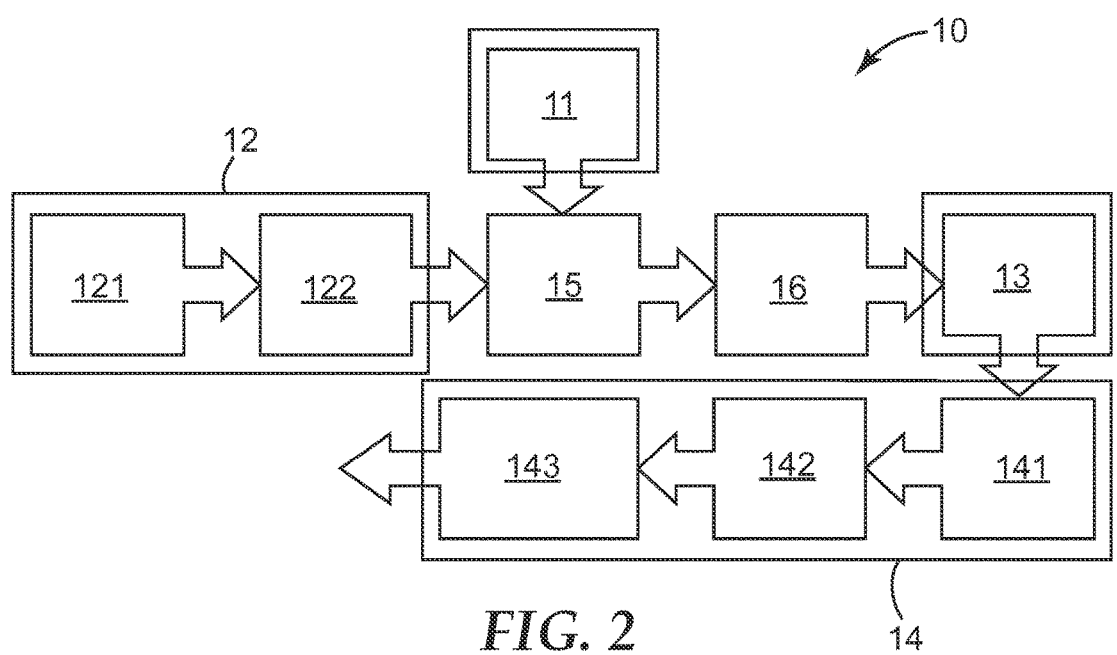
FIG. 2 is a diagram illustrating a further embodiment of the method of the invention.

FIG. 2 illustrates the method 10 in more detail. In step 12 the shape of a patient's teeth are preferably scanned in the step 121. Scanning of a patient's teeth may be performed by directly scanning the natural teeth in the patient's mouth or by scanning a plaster model which is cast from a dental impression of the patient's teeth. The scanned shape of the patient's teeth is provided to CAD (Computer Aided Design) system in step 122 where the dental restoration and/or a blank for making the dental are/is designed. Thus the first and second dimensional information are obtained. The first and second dimensional information are merged in step 15 with the first and second color scheme obtained in step 11 as described in FIG. 1. The first and second color scheme as well as the first and second dimensional information assigned for the first and second color scheme, respectively, in step 16 are used to place an order to a blank manufacturer. After manufacturing of the dental blank in step 13 the dental blank is provided to a CAM (Computer Aided Manufacturing) device in step 141 which mills and/or grinds according to step 142 a dental restoration (step 143).

Figure 3:
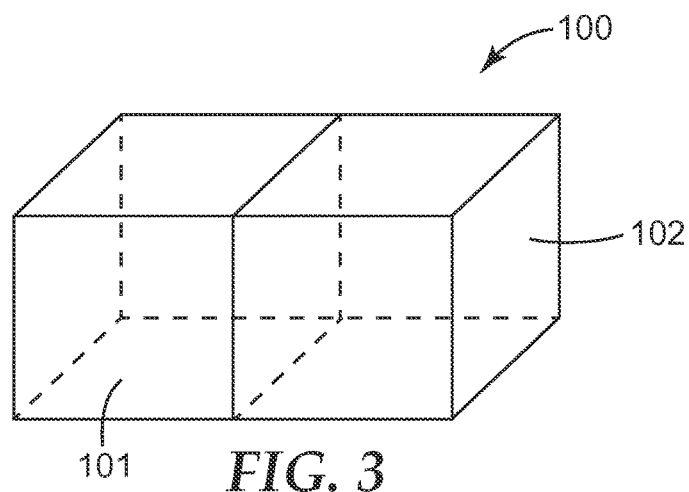
FIG. 3 is a perspective transparent view of a blank obtainable from the method in an embodiment of the invention.

FIGS. 3 to 7 illustrate examples of blanks 100 having at least a first portion 101 based on a first dimensional information according to a first color scheme and a second portion 102 based on a second dimensional information according to a second color scheme. In FIG. 3 the blank 100 has a first and second uniformly colored portion 101, 102. The first and second portion 101, 102 have different colors. The blank 100 is of a cuboid shape and the first and second portion 101, 102 are of generally equal size and shape.

Figure 4:
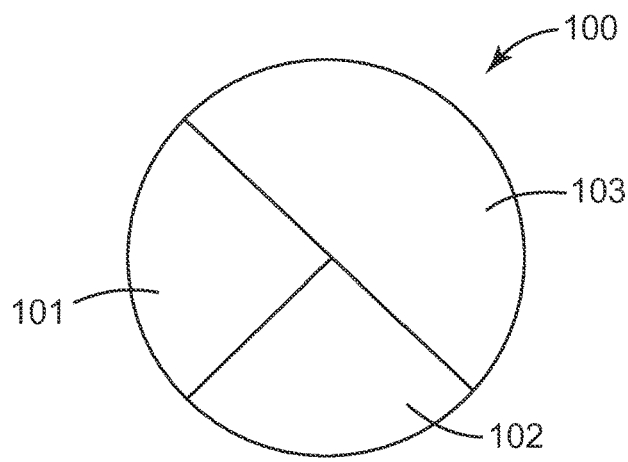
FIG. 4 is a transparent top view of a further blank obtainable from the method in an embodiment of the invention.

In FIG. 4 a blank 100 is illustrated which has a first and second uniformly colored portion 101, 102 and a third portion 103 which is non-uniformly colored according to a color gradient. The third portion 103 in the example is larger than the first and second portion 101, 102. Thus the blank 100 may be used to machine two differently colored dental crowns and a color graded dental bridge.

Figure 5:
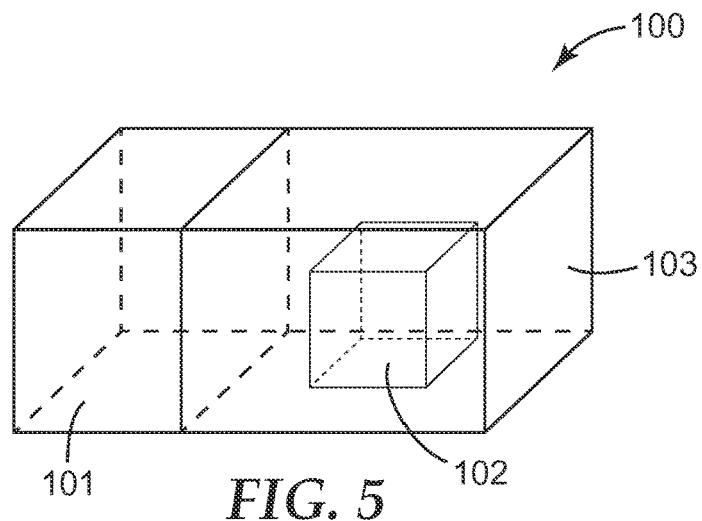
FIGS. 5-7 are perspective transparent views of still further blanks obtainable from the method in an embodiment of the invention.

FIG. 5 illustrates a blank 100 having a first portion 101 which may be uniformly or non-uniformly colored. The first portion 101 has outer boundaries corresponding to a part of the outer boundaries of the blank 100. The blank 100 further has a second portion 102 which is nested within a third portion 103 surrounding the second portion 102. The second and third portion 102, 103 have different colors. Thus a dental restoration may be machined from the second portion 102 only or as an overlap between the second and third portion 102, 103. Accordingly the color of the dental restoration may be controlled by the location at which the dental restoration is machined from the blank.

Figure 6:
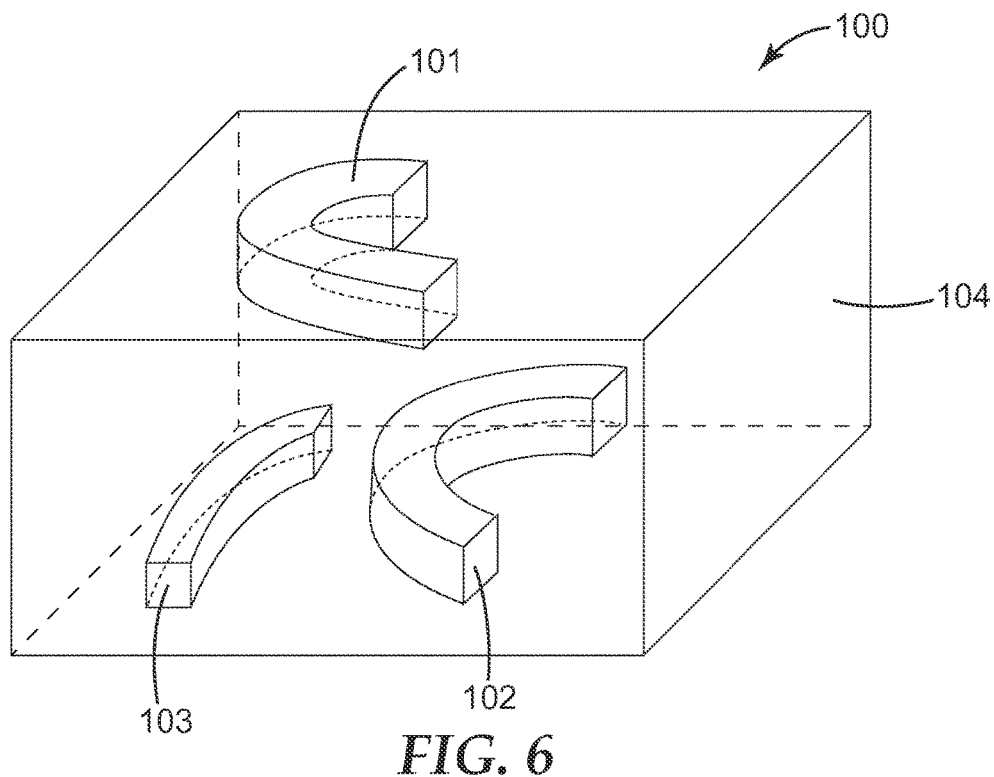

FIG. 6 illustrates a blank 100 having a first, a second and a third portion 101, 102, 103 which in the example each are arch-shaped. The first, second and third portion 101, 102, 103 further may be non-uniformly colored to resemble the color of natural teeth. Further the first, second and third portion 101, 102, 103 are nested separate from each other within a fourth portion 104.

Figure 7:
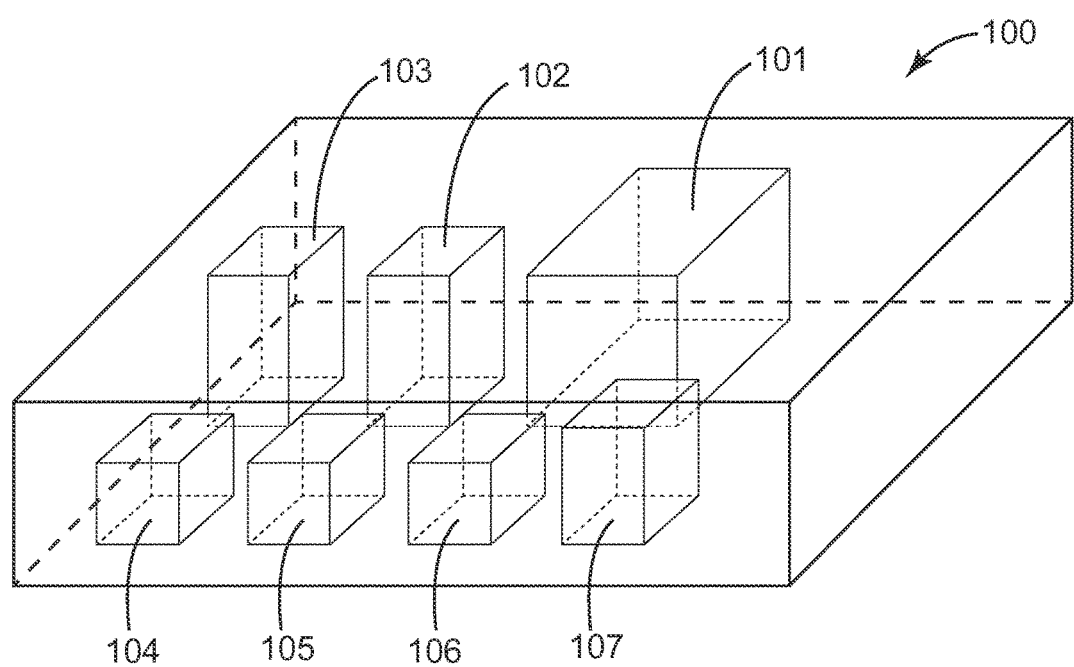

FIG. 7 shows a dental blank 100 having multiple portions 101-107. The skilled person will recognize further possibilities to shape, size and to arrange portions of different colors within a blank.

What is claimed is:

1. A method of making a customized dental blank, comprising:
    providing a dental blank-configurator allowing at least the selection of the first and second color scheme from a plurality of pre-defined color schemes;
    obtaining from a dental practitioner a first color scheme and a different second color scheme as well as a first dimensional information for the first color scheme and a different second dimensional information for the second color scheme, wherein the first and second dimensional information each relate to a size and/or a location within dimensions of the dental blank;
    manufacturing the customized dental blank having a first portion based on the first dimensional information according to the first color scheme and a second portion based on the second dimensional information according to the second color scheme; and
    providing the dental practitioner with the customized dental blank.

2. The method of claim 1, wherein at least one of the first and second color scheme comprises a color gradient or consists of a single color.

3. The method of claim 1, further comprising obtaining first dimensions of the first portion and second dimensions of the second portion from the dental practitioner.

4. The method of claim 1, further comprising obtaining material information from the dental practitioner, wherein the material information relates to a material the dental blank is made of.

5. The method of claim 4, wherein the material is selected from among a ceramic, glass ceramic or composite material, and selected from among zirconia, alumina, lithium disilicate, resin nano ceramic, and hybrid materials.

6. The method of claim 1, comprising obtaining from a plurality of dental practitioners first color schemes and different second color schemes and corresponding first dimensional information and second dimensional information.

7. The method of claim 1, wherein the dental blank-configurator is computer-based.

8. The method of claim 1, further comprising:
    assigning the customized dental blank an individual code based on at least the first and second color scheme and the first and second dimensional information;
    providing the customized dental blank with the individual code in a machine readable form; and
    controlling machining of the blank using machining instructions that are based on the individual code.

9. The method of claim 1, wherein the first portion and the second portion are spaced from each other with a third portion extending between the first portion and the second portion.

10. The method of claim 1, wherein at least one of the first and second portion is/are shaped based on a dental arc or partial dental arc.

11. The method of claim 1, further comprising:
    capturing at least one natural tooth color from a patient's dentition; and
    determining the first and/or second color scheme based on the at least one natural tooth color.

12. A method of making a dental restoration, comprising:
    providing a customized dental blank according to claim 1;
    capturing the shape of at least part of the patient's dentition;
    designing a dental restoration based on the captured shape; and
    machining the dental restoration.

13. A system for making a customized dental blank comprising:
    a scanner for capturing the shape of at least part of a patient's dentition;
    a computer being configured to receive input about a natural tooth color associated to the patient's dentition;
    software configured to receive a first color scheme and a different second color scheme based on the natural tooth color;
    the software being further configured to receive a first dimensional information for the first color scheme and a different second dimensional information for the second color scheme within dimensions of the dental blank;
    the software being further configured to initiate, by data transfer, an order of the customized dental blank based on the first and second color scheme and the first and second dimensional information.

14. The system of claim 13, further comprising a dental blank-configurator allowing at least the selection of the first and second color scheme from a plurality of pre-defined color schemes.

* * * * *